(12) United States Patent
Scarberry (10) Patent No.: US 10,888,266 B2
(45) Date of Patent: Jan. 12, 2021

(54) SLEEP QUALITY AND APNEA HYPOPNEA INDEX MONITORING SYTEM

(71) Applicant: KONINKLIJKE PHILIPS N.V., Eindhoven (NL)

(72) Inventor: Eugene Nelson Scarberry, Trafford, PA (US)

(73) Assignee: Koninklijke Philips N.V., Eindhoven (NL)

( * ) Notice: Subject to any disclaimer, the term of this patent is extended or adjusted under 35 U.S.C. 154(b) by 244 days.

(21) Appl. No.: 16/069,527

(22) PCT Filed: Jan. 12, 2017

(86) PCT No.: PCT/IB2017/050140
§ 371 (c)(1),
(2) Date: Jul. 12, 2018

(87) PCT Pub. No.: WO2017/122138
PCT Pub. Date: Jul. 20, 2017

(65) Prior Publication Data
US 2019/0021654 A1   Jan. 24, 2019

Related U.S. Application Data
(60) Provisional application No. 62/277,647, filed on Jan. 12, 2016.

(51) Int. Cl.
*A61B 5/00*   (2006.01)
*A61B 5/08*   (2006.01)
(Continued)

(52) U.S. Cl.
CPC .......... *A61B 5/4815* (2013.01); *A61B 5/0205* (2013.01); *A61B 5/0402* (2013.01);
(Continued)

(58) Field of Classification Search
CPC .............. A61M 16/00; A61M 16/0066; A61M 16/022; A61M 16/024; A61M 2230/04;
(Continued)

(56) References Cited

U.S. PATENT DOCUMENTS

2005/0061315 A1   3/2005   Lee
2005/0115561 A1   6/2005   Stahmann
(Continued)

FOREIGN PATENT DOCUMENTS

WO   WO2005018737 A1   3/2005
WO   WO2015054134 A1   4/2015

OTHER PUBLICATIONS

Collop NA, Anderson WM, Boehlecke B, et al. Clinical guidelines for the use of unattended portable monitors in the diagnosis of obstructive sleep apnea in adult patients. Portable Monitoring Task Force of the American Academy of Sleep Medicine. J Clin Sleep Med. 2007;3(7):737-747.*

(Continued)

*Primary Examiner* — Joseph D. Boecker
(74) *Attorney, Agent, or Firm* — Michael W. Haas (57) ABSTRACT

Sleep related conditions of a subject are monitored and/or diagnosed based on both sleep quality and apnea hypopnea index. A first sleep test is performed in which a sleep quality of the subject and an apnea-hypopnea index are determined. A determination is made as to whether results of the first sleep test meet a first condition based on both the sleep quality and apnea-hypopnea index of the subject associated with the first sleep test. Responsive to the results of the first sleep test failing to meet the first condition, a recommendation of a treatment for the subject is provided. An efficacy of the treatment is confirmed in a second sleep test involving the treatment by determining whether results of the second sleep test meet the first condition based on both the sleep (Continued)

quality and apnea-hypopnea index of the subject associated with the second sleep test.

15 Claims, 3 Drawing Sheets

(51) Int. Cl.
    *A61M 16/00*     (2006.01)
    *A61B 5/0402*     (2006.01)
    *A61B 5/1455*     (2006.01)
    *A61B 5/0205*     (2006.01)
    *A61B 5/091*     (2006.01)

(52) U.S. Cl.
    CPC ............ *A61B 5/08* (2013.01); *A61B 5/14551* (2013.01); *A61B 5/4818* (2013.01); *A61B 5/4836* (2013.01); *A61B 5/4848* (2013.01); *A61M 16/024* (2017.08); *A61B 5/0816* (2013.01); *A61B 5/091* (2013.01); *A61M 2230/04* (2013.01); *A61M 2230/205* (2013.01); *A61M 2230/42* (2013.01)

(58) Field of Classification Search
    CPC ........ A61M 2230/205; A61M 2230/42; A61B 5/0205; A61B 5/08; A61B 5/0826; A61B 5/091; A61B 5/113; A61B 5/4806; A61B 5/4812; A61B 5/4815; A61B 5/4818; A61B 5/4836; A61B 5/4848
    See application file for complete search history.

(56) References Cited

U.S. PATENT DOCUMENTS

| | | | |
|---|---|---|---|
| 2005/0217674 A1* | 10/2005 | Burton | A61B 5/04 128/204.23 |
| 2010/0049008 A1* | 2/2010 | Doherty | A61M 16/024 600/301 |
| 2011/0306850 A1* | 12/2011 | Hatlestad | A61B 5/0031 600/301 |
| 2013/0046151 A1 | 2/2013 | Bsoul | |
| 2013/0340751 A1* | 12/2013 | D'Angelo | A61M 16/0057 128/202.22 |
| 2014/0046184 A1* | 2/2014 | Heinrich | A61B 5/0064 600/438 |
| 2014/0102454 A1 | 4/2014 | Paul | |
| 2015/0139935 A1 | 5/2015 | Braley | |
| 2015/0223699 A1 | 8/2015 | Yoon | |
| 2015/0313535 A1* | 11/2015 | Alshaer | A61B 5/4812 600/529 |
| 2016/0015917 A1* | 1/2016 | Knepper | A61M 16/024 128/204.23 |
| 2016/0045161 A1* | 2/2016 | Alshaer | A61B 5/087 600/538 |
| 2016/0151603 A1* | 6/2016 | Shouldice | A61M 21/02 600/28 |

OTHER PUBLICATIONS

American Academy of Sleep Medicine, The AASM Manual for the Scoring of Sleep and Associated Events, retrieved from https://aasm.org/clinical-resources/scoring-manual/.*

* cited by examiner

| First sleep test | | |
|---|---|---|
| AHI | sleep quality | Next step for patient |
| poor | poor | treat with airway therapy (ie CPAP) |
| good | poor | refer to sleep specialist |
| good | good | no need to treat do nothing |

| Second sleep test with treatment | | |
|---|---|---|
| AHI | sleep quality | Next step for patient |
| good | good | continue with airway treatment and send home on same treatment |
| good | poor | refer to sleep specialist |

SLEEP QUALITY AND APNEA HYPOPNEA INDEX MONITORING SYTEM

CROSS-REFERENCE TO RELATED APPLICATIONS

This patent application claims the priority benefit under 35 U.S.C. § 371 of international patent application no. PCT/IB2017/050140, filed Jan. 12, 2017, which claims the priority benefit under 35 U.S.C. § 119(e) of U.S. Provisional Application No. 62/277,647 filed on Jan. 12, 2016, the contents of which are herein incorporated by reference.

BACKGROUND OF THE INVENTION

1. Field of the Invention

The present disclosure pertains to systems and methods for monitoring and/or diagnosing sleep related conditions of a subject based on both sleep quality and apnea hypopnea index.

2. Description of the Related Art

Patients in a hospital, as well as in other clinical settings, are typically monitored using a variety of monitoring systems. For example, the current standard for diagnosing sleep disorder breathing involves seven to twenty two sensors, which is not practical in a routine hospital environment. In addition, while measured parameters provide valuable information, when considered individually, they do not provide sufficient information about the condition of the patient in order to optimize treatment of the patient for multiple disorders. If a patient is given an optimal treatment, the likelihood that the patient will need to be readmitted in a relatively short time after being discharged from the hospital decreases. It should be noted that because readmission of a patient for the same condition within a certain number of days following discharge is generally not reimbursed by U.S. insurance policies, readmission is costly to the hospital. As a result, hospitals endeavor to avoid such readmissions. In sum, known systems that monitor the varied health-related parameters of a patient lack a sufficient level of sophistication needed in order optimize the treatment of the patient thereby avoiding unreimbursed hospital readmissions.

SUMMARY OF THE INVENTION

Accordingly, one or more aspects of the present disclosure relate to a system configured for monitoring and/or diagnosing sleep related conditions of a subject based on both sleep quality and apnea hypopnea index. The system comprises one or more sleep quality sensors, one or more respiratory sensors, one or more hardware processors, and/or other components. The one or more sleep quality sensors are configured to provide sleep quality signals conveying information related to a sleep quality measurement of the subject. The one or more respiratory sensors are configured to provide respiratory signals conveying information related to a breathing measurement of the subject. The one or more hardware processors are configured by machine-readable instructions to: receive, in connection with a first sleep test, the sleep quality signals from the one or more sleep quality sensors and the respiratory signals from the one or more respiratory sensors; determine a sleep quality of the subject, in connection with the first sleep test, based on the sleep quality signals; determine an apnea-hypopnea index of the subject, in connection with the first sleep test, based on the respiratory signals; determine whether results of the first sleep test meet a first condition based on both the sleep quality and apnea-hypopnea index of the subject associated with the first sleep test; and responsive to the results of the first sleep test failing to meet the first condition, provide a recommendation of a treatment for the subject and confirm an efficacy of the treatment in a second sleep test involving the treatment. The efficacy is confirmed by: receiving, in connection with a second sleep test, the sleep quality signals from the one or more sleep quality sensors and the respiratory signals from the one or more respiratory sensors; determining a sleep quality of the subject, in connection with the second sleep test, based on the sleep quality signals; determining an apnea-hypopnea index of the subject, in connection with the first sleep test, based on the respiratory signals; and determining whether results of the second sleep test meet the first condition based on both the sleep quality and apnea-hypopnea index of the subject associated with the second sleep test.

Another aspect of the present disclosure relates to a method for monitoring and/or diagnosing sleep related conditions of a subject based on both sleep quality and apnea hypopnea index. The method comprises: receiving, in connection with a first sleep test, sleep quality signals conveying information related to a sleep quality measurement of the subject and respiratory signals conveying information related to a breathing measurement of the subject; determining a sleep quality of the subject, in connection with the first sleep test, based on the sleep quality signals; determining an apnea-hypopnea index of the subject, in connection with the first sleep test, based on the respiratory signals; determining whether results of the first sleep test meet a first condition based on both the sleep quality and apnea-hypopnea index of the subject associated with the first sleep test; responsive to the results of the first sleep test failing to meet the first condition, providing a recommendation of a treatment for the subject; and confirming an efficacy of the treatment in a second sleep test involving the treatment. The efficacy is confirmed by: receiving, in connection with a second sleep test, the sleep quality signals from the one or more sleep quality sensors and the respiratory signals from the one or more respiratory sensors; determining a sleep quality of the subject, in connection with the second sleep test, based on the sleep quality signals; determining an apnea-hypopnea index of the subject, in connection with the first sleep test, based on the respiratory signals; and determining whether results of the second sleep test meet the first condition based on both the sleep quality and apnea-hypopnea index of the subject associated with the second sleep test.

Still another aspect of the present disclosure relates to a system configured for monitoring and/or diagnosing sleep related conditions of a subject based on both sleep quality and apnea hypopnea index. The system comprises: means for receiving, in connection with a first sleep test, sleep quality signals conveying information related to a sleep quality measurement of the subject and respiratory signals conveying information related to a breathing measurement of the subject; means for determining a sleep quality of the subject, in connection with the first sleep test, based on the sleep quality signals; means for determining an apnea-hypopnea index of the subject, in connection with the first sleep test, based on the respiratory signals; means for determining whether results of the first sleep test meet a first condition based on both the sleep quality and apnea-hypopnea index of the subject associated with the first sleep test;

means for, responsive to the results of the first sleep test failing to meet the first condition, providing a recommendation of a treatment for the subject; and means for confirming an efficacy of the treatment in a second sleep test involving the treatment. The efficacy is confirmed by: receiving, in connection with a second sleep test, the sleep quality signals from the one or more sleep quality sensors and the respiratory signals from the one or more respiratory sensors; determining a sleep quality of the subject, in connection with the second sleep test, based on the sleep quality signals; determining an apnea-hypopnea index of the subject, in connection with the first sleep test, based on the respiratory signals; and determining whether results of the second sleep test meet the first condition based on both the sleep quality and apnea-hypopnea index of the subject associated with the second sleep test.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
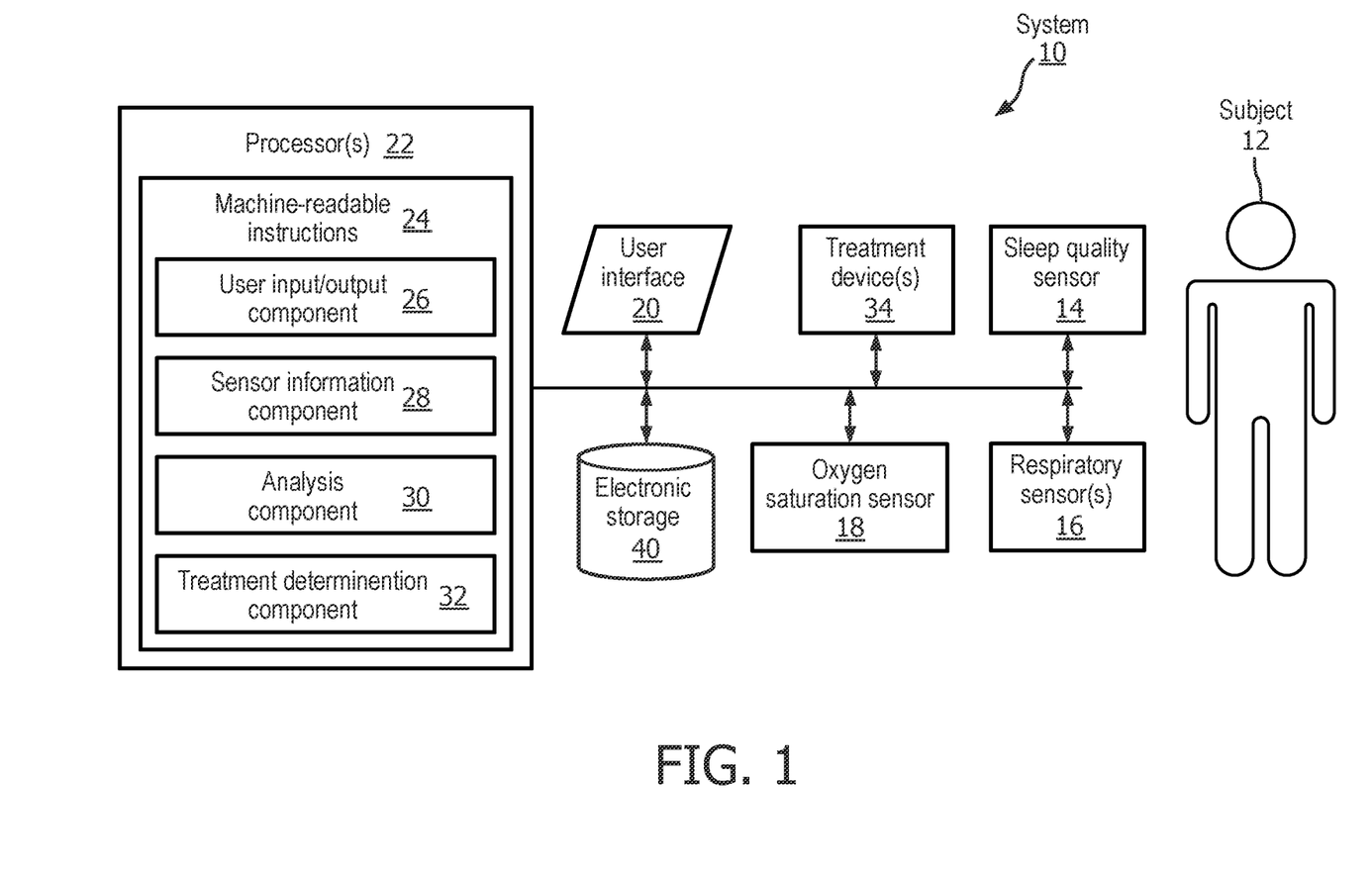
FIG. 1 illustrates a system configured for monitoring and/or diagnosing sleep related conditions of a subject based on both sleep quality and apnea hypopnea index, in accordance with one or more embodiments.

FIG. 1 illustrates a system 10 configured for monitoring and/or diagnosing sleep related conditions of a subject 12 based on both sleep quality and apnea hypopnea index (AHI), in accordance with one or more embodiments. For purposes of this disclosure, the term "sleep quality" may refer to a measure of overall stable sleep, while the term "AHI" may refer to any form of measuring disrupted sleep due to an unstable airway (e.g., respiratory disturbance index (RDI), probability of obstructive sleep apnea (OSA), and/or other measurements).

Commonly, when a subject (e.g., subject 12) is admitted to a hospital, he/she is hooked up to an electrocardiogram (ECG) monitor and, occasionally, an oxygen saturation ($S_PO_2$) monitor, primarily in order to detect arrhythmias to ensure the subject is not going to have a heart attack or showing any ventricular problems that could cause cardiac arrest. According to exemplary embodiments, from a raw ECG signal, a probability of sleep apnea (or apnea-hypopnea index) may be determined as well as sleep quality. In embodiments including oxygen saturation measurement, respiratory problems may also be identified. Contrasted with standard sleep monitoring for sleep disorder breathing, exemplary embodiments have reduced cost at least because there are significantly less sensors. That is, there are only the standard monitoring sensors (e.g., ECG and/or $S_PO_2$), according to some embodiments. In standard sleep monitoring, there are commonly electrodes on the subject's head measuring brain waves and electrodes on the subject's feet measuring leg kicks—all of which are generally highly impractical for a standard hospital-monitored subject. Accordingly, exemplary embodiments utilize what is most typically already available—the ECG electrodes that are routinely connected to the subject upon hospital admission—and identify sleep disorder breathing. In situations where disruptive breathing and quality of sleep is so poor therapy is needed, exemplary embodiments provide an ability to monitor whether the therapy is valid.

Accordingly, according to one or more embodiments, system 10 includes one or more of one or more sleep quality sensors 14, one or more respiratory sensors 16, one or more oxygen saturation sensors 18, one or more user interfaces 20, one or more processors 22, and/or other components.

Sleep quality sensor(s) 14 are configured to provide sleep quality signals conveying information related to a sleep quality measurement of the subject. Generally speaking, sleep quality may be described subjectively and/or objectively. A subjective description may include tiredness on waking and throughout the day or feeling rested and restored on waking. An objective description may include the number of awakenings experienced in the night. Awakenings may be determined by motion detection and/or other techniques. In some embodiments, sleep quality sensor(s) may include an accelerometer, a visual motion detector, and/or other sensors configured to detect motion. An objective description may include efficiency of sleep. In some embodiments, sleep quality sensor(s) 14 include an electrocardiogram (ECG) configured to monitor heart activity. In such embodiments, the sleep quality signal may convey information related to heart activity of the subject. The heart activity of the subject may be used to determine one or more indices for sleep quality. Examples of such indices may include one or more of sleep efficiency index, delta-sleep efficiency index, sleep onset latency, respiratory arousals, and/or other indices of sleep quality. Other sensors useful for determining sleep quality are contemplated as sleep quality sensor(s) 14 and are within the scope of the disclosure.

Respiratory sensor(s) 16 are configured to provide respiratory signals conveying information related to a breathing measurement of the subject. The breathing measurement may convey inspiration and/or expiration volume as a function of time, a number of breaths as a function of time, and/or other breathing measurements. In some embodiments, respiratory sensor(s) 16 may include one or more of a flow meter, an effort belt, a chest impediment, a thermocouple, an air pressure sensor, and/or other sensors suitable for measuring respiration of the subject.

Oxygen saturation sensor(s) 18 may be configured to provide oxygen saturation signals conveying information related to an oxygen saturation ($S_PO_2$) of the subject. In some embodiments, oxygen saturation sensor(s) 18 may include one or more of a pulse oximeter and/or other sensors suitable for measuring oxygen saturation.

Figure 2:
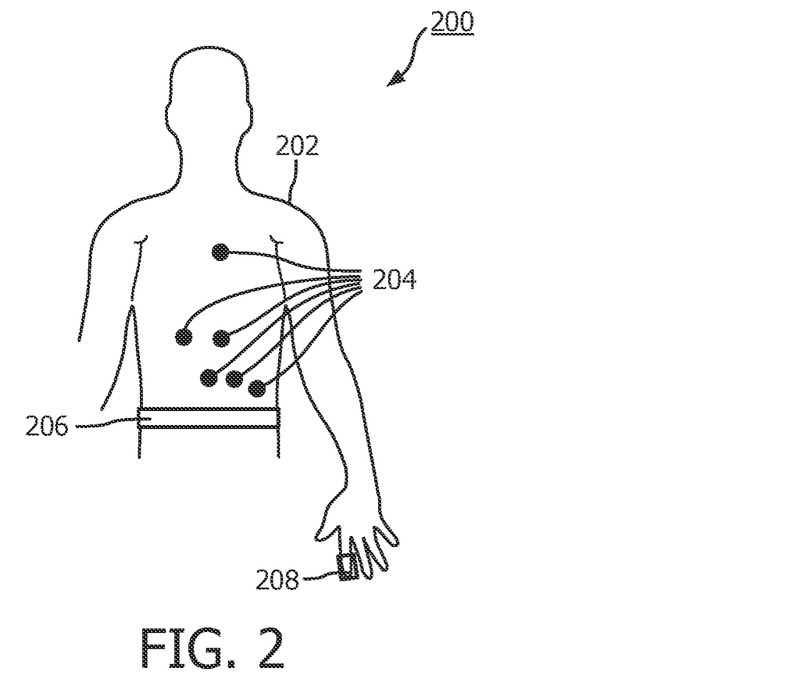
FIG. 2 illustrates exemplary sensor configuration, in accordance with one or more embodiments.

FIG. 2 illustrates exemplary sensor configuration 200, in accordance with one or more embodiments. As shown in FIG. 2, a subject 202 may be fitted with one or more sensors. Such sensors may include one or more of electrocardiogram (ECG) sensors 204, effort belt 206, pulse oximeter 208, and/or other sensors. ECG sensors 204 are disposed at one or more positions near the heart of subject 202. In some embodiments, sleep quality sensor(s) 14 (shown in FIG. 1) includes an electrocardiogram (ECG) that is the same as or similar to ECG sensors 204. Effort belt 206 is disposed about the chest of subject 202. In some embodiments, respiratory sensor(s) 16 (shown in FIG. 1) includes an effort belt that is the same as or similar to effort belt 206. Pulse oximeter 208 is disposed on a finger of subject 202. In some embodiments, oxygen saturation sensor(s) 18 (shown in FIG. 1) includes a pulse oximeter that is the same as or similar to pulse oximeter 208. While sensor configuration 200 shows three specific sensors, this is not intended to be limiting as other configurations are contemplated and are within the scope of the disclosure. For example, sensor configuration 200 may include one or more additional sensors not described, and/or without one or more of the sensors discussed.

User interface(s) 20 is configured to provide an interface between system 10 and caregivers, subject 12, and/or other users through which caregivers, subject 12, and/or other users may provide information to and receive information from system 10. This enables data, cues, results, and/or instructions and any other communicable items, collectively referred to as "information," to be communicated between a user (e.g., a caregiver, subject 12, and/or other users) and processor 18, and/or other components of system 10. For example, sleep quality information, apnea-hypopnea index, oxygen saturation, and/or other information about subject 12 may be communicated from a caregiver to system 10 via user interface(s) 20.

Examples of interface devices suitable for inclusion in user interface(s) 20 comprise a graphical user interface, a display, a touchscreen, a keypad, buttons, switches, a keyboard, knobs, levers, speakers, a microphone, an indicator light, an audible alarm, a printer, a haptic feedback device, and/or other interface devices. In some embodiments, user interface(s) 20 comprises a plurality of separate interfaces. For example, user interface(s) 20 may comprise a plurality of different interfaces associated with a plurality of computing devices associated with different caregivers. User interface(s) 20 is configured such that the plurality of caregivers may provide information to and receive information from (e.g., treatment information, etc.) system 10 via the individual ones of the plurality of user interfaces. In some embodiments, user interface(s) 20 comprises at least one interface that is provided integrally with processor 18 and/or other components of system 10.

It is to be understood that other communication techniques, either hard-wired or wireless, are also contemplated by the present disclosure as user interface(s) 20. For example, the present disclosure contemplates that user interface(s) 20 may be integrated with a removable storage interface provided by electronic storage 40. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface(s) 20 comprise, but are not limited to, an RS-232 port, RF link, an IR link, modem (telephone, cable or other). In short, any technique for communicating information with system 10 is contemplated by the present disclosure as user interface(s) 20.

Processor(s) 22 are configured to provide information processing capabilities in system 10. As such, processor(s) 22 may comprise one or more of a digital processor, an analog processor, a digital circuit designed to process information, an analog circuit designed to process information, a state machine, and/or other mechanisms for electronically processing information. Although processor(s) 22 is shown in FIG. 1 as a single entity, this is for illustrative purposes only. In some embodiments, processor(s) 22 may comprise a plurality of processing units. These processing units may be physically located within the same device, or processor(s) 22 may represent processing functionality of a plurality of devices operating in coordination.

As shown in FIG. 1, processor(s) 22 are configured by machine-readable instructions 24. Machine-readable instructions 24 may be executed by processor(s) 22 to cause processor(s) 22 to perform one or more functions. Machine-readable instructions 22 may include one or more of a user input/output component 26, a sensor information component 28, an analysis component 30, a treatment determination component 32, and/or other components. Processor(s) 22 may be configured to execute components 26, 28, 30, 32, and/or other components by software; hardware; firmware; some combination of software, hardware, and/or firmware; and/or other mechanisms for configuring processing capabilities on processor(s) 22.

It should be appreciated that although components 26, 28, 30, and 32 are illustrated in FIG. 1 as being co-located within a single processing unit, in embodiments in which processor(s) 22 comprises multiple processing units, one or more of components 26, 28, 30, and/or 32 may be located remotely from the other components. The description of the functionality provided by the different components 26, 28, 30, and/or 32 described herein is for illustrative purposes, and is not intended to be limiting, as any of components 26, 28, 30, and/or 32 may provide more or less functionality than is described. For example, one or more of components 26, 28, 30, and/or 32 may be eliminated, and some or all of its functionality may be provided by other components 26, 28, 30, and/or 32. As another example, processor(s) 22 may be configured to execute one or more additional components that may perform some or all of the functionality attributed below to one of components 26, 28, 30, and/or 32.

User input/output component 26 is configured to facilitate entry and/or selection of information by subject 12, caregivers, and/or other users. User input/output component 26 facilitates entry and/or selection of information via user interface(s) 20 and/or other interface devices. For example, user input/output component 26 may cause user interface(s) 20 to display one or more views of a graphical user interface to a caregiver which facilitate entry and/or selection of information by the caregiver. In some embodiments, user input/output component 26 is configured to facilitate entry and/or selection of information via one or more user interfaces 16 associated with one or more caregivers. In some embodiments, user input/output component 26 is be configured to facilitate entry and/or selection of information through a website, a mobile app, a bot through which text messages and/or emails are sent, and/or via other methods. In some embodiments, user input/output component 26 is configured to prompt subject 12, caregivers, and/or other users to answer specific questions, and/or provide other information. In some embodiments, user input/output component 26 is configured to associate a time of day, a duration of time, and/or other time information with the entered and/or selected information.

Sensor information component 28 is configured to receive one or more signals from one or more sensors. Such signal may be received in connection with one or more sleep tests. In some embodiments, sensor information component 28 is configured to receive one or more of sleep quality signals from sleep quality sensor(s) 14, respiratory signals from respiratory sensor(s) 16, oxygen saturation signals from oxygen saturation sensor(s) 18, and/or other signals.

Analysis component 30 is configured to determine various quantities associated with subject 12. Such determinations may be made in connection with one or more sleep tests. The quantities may be determined based on information conveyed by signals received by sensor information component 28. In some embodiments, analysis component 30 is configured to determine a sleep quality of subject 12. The sleep quality may be determined based on the sleep quality signals. In some embodiments, analysis component 30 is configured to determine an apnea-hypopnea index of subject 12. The apnea-hypopnea index may be determined based on the respiratory signals. In some embodiments, analysis component 30 is configured to determine an oxygen saturation ($S_PO_2$) of subject 12. The oxygen saturation may be determined based on the oxygen saturation signals.

In some embodiments, analysis component 30 is configured to determine whether results of a given sleep test meet a first condition. The determination of whether results of the given sleep test meet the first condition may be based on one or more of the sleep quality of subject 12, the apnea-hypopnea index of subject 12, the oxygen saturation of subject 12, neuro arousals connected to the respirator effort, and/or other information. In some embodiments, a first condition is met when two or more results of the given sleep test are considered "good".

Treatment determination component 32 is configured to provide a recommendation of a treatment for subject 12. Such determination may be made responsive to the results of a given sleep test failing to meet the first condition (as determined by analysis component 30. The treatment may be provided by one or more treatment devices 34. In some embodiments, treatment device(s) 34 may include one or more of a smart (e.g., auto-titrating) continuous positive airway pressure (CPAP) device, bi-level PAP, volume-guaranteed PAP, and/or other devices that treat sleep disordered breathing.

Referring again to analysis component 30, it may be configured to confirm an efficacy of the treatment in a second (or successive) sleep test involving the treatment. Such confirmation may be performed in conjunction with one or more other machine-readable instruction components. For example, in exemplary embodiments, confirming the efficacy of the treatment may include: receiving, in connection with a second sleep test, the sleep quality signals from the one or more sleep quality sensors and the respiratory signals from the one or more respiratory sensors; determining a sleep quality of the subject, in connection with the second sleep test, based on the sleep quality signals; determining an apnea-hypopnea index of the subject, in connection with the first sleep test, based on the respiratory signals; and determining whether results of the second sleep test meet the first condition based on both the sleep quality and apnea-hypopnea index of the subject associated with the second sleep test.

Figure 3:
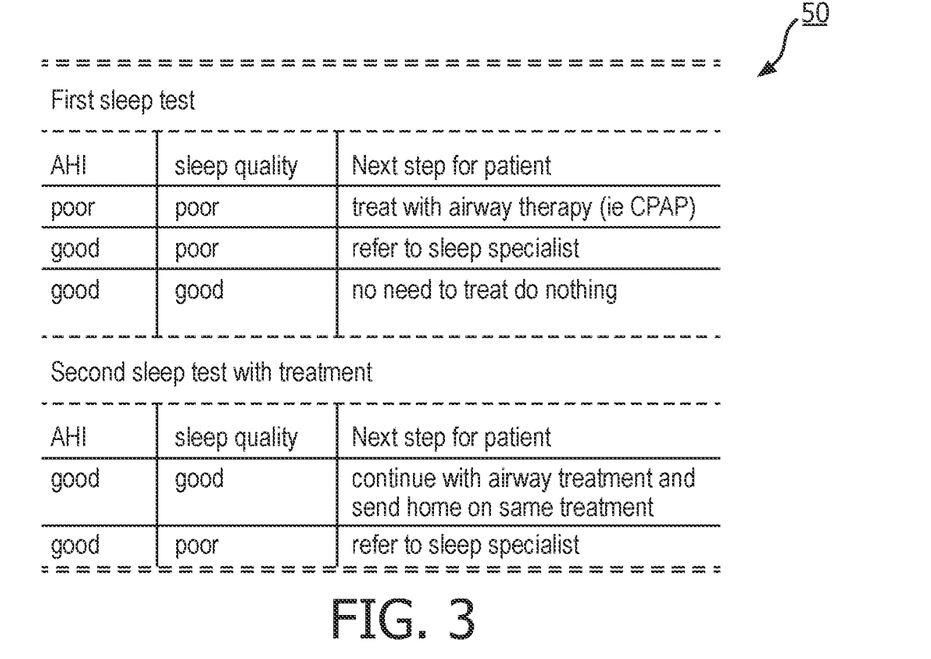
FIG. 3 illustrates a condition matrix, in accordance with one or more embodiments.

FIG. 3 illustrates a condition matrix 50, in accordance with one or more embodiments. The condition matrix 50 shows various combinations of sleep test outcomes. More specifically, condition matrix 50 shows combinations of AHI and sleep quality being either "poor" or "good." According to some embodiments, in connection with a first sleep test, if both AHI and sleep quality are poor, then subject 12 is treated with an airway treatment (e.g., CPAP); if AHI is good and sleep quality is poor, then subject 12 is referred to a sleep specialist; and if both AHI and sleep quality are good, then there is no need for treatment. In connection with a second sleep test where treatment is provided to subject 12 in response to the outcome of the first sleep test, if AHI is good and sleep quality is poor, then subject 12 is referred to a sleep specialist; and if both AHI and sleep quality are good, then the provided treatment is continued and may be used in a home setting, in accordance with some embodiments.

Electronic storage 40 comprises electronic storage media that electronically stores information. The electronic storage media of electronic storage 40 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 40 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 40 may store software algorithms, information determined by processor(s) 22, information received via user interface(s) 20 and/or external computing systems, information received from sleep quality sensor(s) 14, information received from respiratory sensor(s) 16, information received from saturation sensor(s) 18, and/or other information that enables system 10 to function as described herein. Electronic storage 40 may be (in whole or in part) a separate component within system 10, or electronic storage 40 may be provided (in whole or in part) integrally with one or more other components of system 10 (e.g., user interface(s) 20, processor(s) 22).

Figure 4:
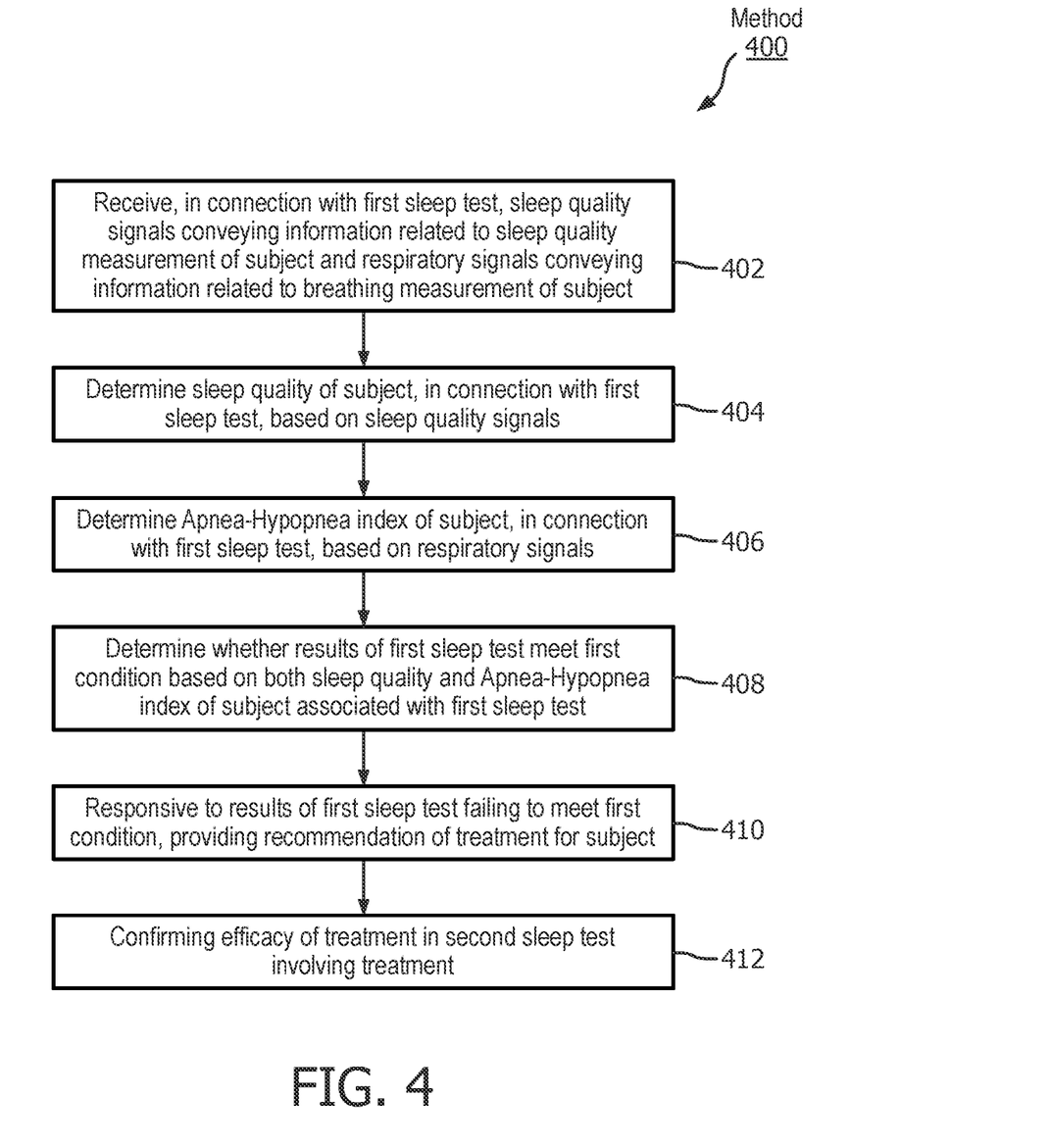
FIG. 4 illustrates a method for monitoring and/or diagnosing sleep related conditions of a subject based on both sleep quality and apnea hypopnea index, in accordance with one or more embodiments.

FIG. 4 illustrates a method 400 for monitoring and/or diagnosing sleep related conditions of a subject based on both sleep quality and apnea hypopnea index, in accordance with one or more embodiments. The operations of method 400 presented below are intended to be illustrative. In some embodiments, method 400 may be accomplished with one or more additional operations not described, and/or without one or more of the operations discussed. Additionally, the order in which the operations of method 400 are illustrated in FIG. 4 and described below is not intended to be limiting.

In some embodiments, one or more operations of method 400 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 400 in response to instructions stored electronically on an electronic storage medium. The one or more processing devices may include one or more devices configured through hardware, firmware, and/or software to be specifically designed for execution of one or more of the operations of method 400.

At an operation 402, in connection with a first sleep test, sleep quality signals and respiratory signals are received. The sleep quality signals may convey information related to a sleep quality measurement of the subject. The respiratory signals may convey information related to a breathing measurement of the subject. Operation 402 may be performed by one or more processors configured by a machine-readable instruction component that is the same as or similar to sensor information component 28 (shown in FIG. 1 and described herein), in accordance with one or more embodiments.

At an operation 404, in connection with the first sleep test, a sleep quality of the subject is determined based on the sleep quality signals. Operation 404 may be performed by one or more processors configured by a machine-readable instruction component that is the same as or similar to analysis component 30 (shown in FIG. 1 and described herein), in accordance with one or more embodiments.

At an operation 406, in connection with the first sleep test, an apnea-hypopnea index of the subject is determined based on the respiratory signals. Operation 406 may be performed by one or more processors configured by a machine-readable instruction component that is the same as or similar to analysis component 30 (shown in FIG. 1 and described herein), in accordance with one or more embodiments.

At an operation 408, a determination is made as to whether results of the first sleep test meet a first condition based on both the sleep quality and apnea-hypopnea index of the subject associated with the first sleep test. Operation 408 may be performed by one or more processors configured by a machine-readable instruction component that is the same as or similar to analysis component 30 (shown in FIG. 1 and described herein), in accordance with one or more embodiments.

At an operation 410, responsive to the results of the first sleep test failing to meet the first condition, a recommendation is provided of a treatment for the subject. Operation 410 may be performed by one or more processors configured by a machine-readable instruction component that is the same as or similar to treatment determination component 32 (shown in FIG. 1 and described herein), in accordance with one or more embodiments.

At an operation 412, an efficacy of the treatment in a second sleep test involving the treatment is confirmed. In some embodiments, the efficacy is confirmed by: receiving, in connection with a second sleep test, the sleep quality signals from the one or more sleep quality sensors and the respiratory signals from the one or more respiratory sensors; determining a sleep quality of the subject, in connection with the second sleep test, based on the sleep quality signals; determining an apnea-hypopnea index of the subject, in connection with the first sleep test, based on the respiratory signals; and determining whether results of the second sleep test meet the first condition based on both the sleep quality and apnea-hypopnea index of the subject associated with the second sleep test. Operation 402 may be performed by one or more processors configured by one or more machine-readable instruction components that is/are the same as or similar to one or more of sensor information component 28, analysis component 30, and/or treatment determination component 32 (shown in FIG. 1 and described herein), in accordance with one or more embodiments.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the disclosure has been described in detail for the purpose of illustration based on what is currently considered to be the most practical and preferred embodiments, it is to be understood that such detail is solely for that purpose and that the disclosure is not limited to the disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system configured for monitoring and/or diagnosing sleep related conditions of a subject based on both a sleep quality and an apnea hypopnea index, the system comprising:
    (a) one or more sleep quality sensors configured to provide sleep quality signals conveying information related to a sleep quality measurement of the subject;
    (b) one or more respiratory sensors configured to provide respiratory signals conveying information related to a breathing measurement of the subject; and
    (c) one or more hardware processors configured by machine-readable instructions to:
        (1) receive, in connection with a first sleep test, the sleep quality signals from the one or more sleep quality sensors and the respiratory signals from the one or more respiratory sensors,
        (2) determine the sleep quality of the subject, in connection with the first sleep test, based on the sleep quality signals,
        (3) determine the apnea-hypopnea index of the subject, in connection with the first sleep test, based on the respiratory signals,
        (4) determine whether results of the first sleep test meet a first condition based on both the sleep quality and the apnea-hypopnea index of the subject associated with the first sleep test,
        (5) responsive to the results of the first sleep test failing to meet the first condition, provide a recommendation for the subject, wherein providing the recommendation for the subject comprises:
responsive to the apnea-hypopnea index of the subject not meeting a first threshold and the sleep quality of the subject not meeting a second threshold, providing an airway therapy treatment, and
responsive to the apnea-hypopnea index of the subject meeting the first threshold and the sleep quality of the subject not meeting the second threshold, providing a referral to a sleep specialist, and
(6) confirm an efficacy of the treatment in a second sleep test involving the treatment by:
(i) receiving, in connection with the second sleep test, the sleep quality signals from the one or more sleep quality sensors and the respiratory signals from the one or more respiratory sensors,
(ii) determining a second sleep quality of the subject, in connection with the second sleep test, based on the sleep quality signals,
(iii) determining a second apnea-hypopnea index of the subject, in connection with the second sleep test, based on the respiratory signals, and
(iv) determining whether results of the second sleep test meet the first condition based on both the second sleep quality and the second apnea-hypopnea index of the subject associated with the second sleep test.

2. The system of claim 1, wherein the one or more sleep quality sensors include an electrocardiogram (ECG) configured to monitor heart activity, and wherein the sleep quality signal conveys information related to heart activity of the subject.

3. The system of claim 1, further comprising:
one or more oxygen saturation sensors configured to provide oxygen saturation signals conveying information related to an oxygen saturation ($S_PO_2$) of the subject.

4. The system of claim 3, wherein the one or more hardware processors are further configured by machine-readable instructions to:
receive, in connection with the first sleep test, the oxygen saturation signals from the one or more oxygen saturation sensors; and
determine an oxygen saturation of the subject, in connection with the first sleep test, based on the oxygen saturation signals, wherein determining whether the results of the first sleep test meet the first condition is further based on the oxygen saturation of the subject.

5. The system of claim 1, wherein the treatment includes utilizing a continuous positive airway pressure (CPAP) device.

6. A method for monitoring and/or diagnosing sleep related conditions of a subject based on both a sleep quality and an apnea hypopnea index, the method comprising:
(a) receiving, in connection with a first sleep test, sleep quality signals from one or more sleep quality sensors conveying information related to a sleep quality measurement of the subject and respiratory signals from one or more respiratory sensors conveying information related to a breathing measurement of the subject;
(b) determining the sleep quality of the subject, in connection with the first sleep test, based on the sleep quality signals;
(c) determining the apnea-hypopnea index of the subject, in connection with the first sleep test, based on the respiratory signals;
(d) determining whether results of the first sleep test meet a first condition based on both the sleep quality and the apnea-hypopnea index of the subject associated with the first sleep test;
(e) responsive to the results of the first sleep test failing to meet the first condition, providing a recommendation for the subject, wherein providing the recommendation for the subject comprises:
responsive to the apnea-hypopnea index of the subject not meeting a first threshold and the sleep quality of the subject not meeting a second threshold, providing an airway therapy treatment, and
responsive to the apnea-hypopnea index of the subject meeting the first threshold and the sleep quality of the subject not meeting the second threshold, providing a referral to a sleep specialist; and
(f) confirming an efficacy of the treatment in a second sleep test involving the treatment by:
(1) receiving, in connection with a second sleep test, the sleep quality signals from the one or more sleep quality sensors and the respiratory signals from the one or more respiratory sensors,
(2) determining a second sleep quality of the subject, in connection with the second sleep test, based on the sleep quality signals,
(3) determining a second apnea-hypopnea index of the subject, in connection with the second sleep test, based on the respiratory signals, and
(4) determining whether results of the second sleep test meet the first condition based on both the second sleep quality and the second apnea-hypopnea index of the subject associated with the second sleep test.

7. The method of claim 6, wherein the sleep quality signal conveys information related to heart activity of the subject.

8. The method of claim 6, further comprising: receiving, in connection with the first sleep test, oxygen saturation signals conveying information related to an oxygen saturation ($S_PO_2$) of the subject.

9. The method of claim 8, further comprising: determining an oxygen saturation of the subject, in connection with the first sleep test, based on the oxygen saturation signals, wherein determining whether the results of the first sleep test meet the first condition is further based on the oxygen saturation of the subject.

10. The method of claim 6, wherein the treatment includes utilizing a continuous positive airway pressure (CPAP) device.

11. A system configured for monitoring and/or diagnosing sleep related conditions of a subject based on both a sleep quality and an apnea hypopnea index, the system comprising:
a processor having a sensor information component configured to receive, in connection with a first sleep test, sleep quality signals from one or more sleep quality sensors conveying information related to a sleep quality measurement of the subject and respiratory signals from one or more respiratory sensors conveying information related to a breathing measurement of the subject;
a processor having an analysis component configured to determine:
the sleep quality of the subject, in connection with the first sleep test, based on the sleep quality signals,
the apnea-hypopnea index of the subject, in connection with the first sleep test, based on the respiratory signals, and whether results of the first sleep test meet a first condition based on both the sleep quality and the apnea-hypopnea index of the subject associated with the first sleep test;

a processor having an treatment determination component configured to provide, responsive to the results of the first sleep test failing to meet the first condition, providing a recommendation for the subject, wherein responsive to the apnea-hypopnea index of the subject not meeting a first threshold and the sleep quality of the subject not meeting a second threshold, the provided recommendation is an airway therapy treatment, and- responsive to the apnea-hypopnea index of the subject meeting the first threshold and the sleep quality of the subject not meeting the second threshold, the provided recommendation is a referral to a sleep specialist, wherein the analysis component is further configured to confirm an efficacy of the treatment in a second sleep test involving the treatment by:

(1) receiving, in connection with a second sleep test, the sleep quality signals from the one or more sleep quality sensors and the respiratory signals from the one or more respiratory sensors, (2) determining a second sleep quality of the subject, in connection with the second sleep test, based on the sleep quality signals, (3) determining a second apnea-hypopnea index of the subject, in connection with the second sleep test, based on the respiratory signals, and (4) determining whether results of the second sleep test meet the first condition based on both the second sleep quality and the second apnea-hypopnea index of the subject associated with the second sleep test.

12. The system of claim 11, wherein the sleep quality signal conveys information related to heart activity of the subject.

13. The system of claim 11, wherein the sensor information component is further configured to receive, in connection with the first sleep test, oxygen saturation signals conveying information related to an oxygen saturation ($S_PO_2$) of the subject.

14. The system of claim 13, wherein the analysis component is further-configured to determine an oxygen saturation of the subject, in connection with the first sleep test, based on the oxygen saturation signals, wherein determining whether the results of the first sleep test meet the first condition is further based on the oxygen saturation of the subject.

15. The system of claim 11, wherein the treatment includes utilizing a continuous positive airway pressure (CPAP) device.

* * * * *